United States Patent
Barbere

[11] Patent Number: 6,066,157
[45] Date of Patent: *May 23, 2000

[54] ANCHOR JOINT FOR COAXIAL BALLOON DILATATION CATHETER

[75] Inventor: Michael D. Barbere, Dunstable, Mass.

[73] Assignee: Medtronics AVE, Inc., Santa Rose, Calif.

[*] Notice: This patent issued on a continued prosecution application filed under 37 CFR 1.53(d), and is subject to the twenty year patent term provisions of 35 U.S.C. 154(a)(2).

[21] Appl. No.: 09/154,616

[22] Filed: Sep. 16, 1998

[51] Int. Cl.⁷ .................................................. A61M 29/00
[52] U.S. Cl. .............................. 606/194; 606/192; 604/96
[58] Field of Search .................................. 606/194, 192, 606/108; 604/96

[56] References Cited

U.S. PATENT DOCUMENTS

| | | |
|---|---|---|
| 3,543,759 | 12/1970 | McWhorter . |
| 4,024,873 | 5/1977 | Antoshkiw et al. . |
| 4,261,339 | 4/1981 | Hanson et al. . |
| 4,323,071 | 4/1982 | Simpson et al. . |
| 4,327,709 | 5/1982 | Hanson et al. . |
| 4,346,698 | 8/1982 | Hanson et al. . |
| 4,638,805 | 1/1987 | Powell . |
| 4,646,742 | 3/1987 | Packard et al. . |
| 4,665,925 | 5/1987 | Millar ........................................ 604/96 |
| 4,689,041 | 8/1997 | Corday et al. . |
| 4,702,252 | 10/1987 | Brooks et al. . |
| 4,794,928 | 1/1989 | Kletschka . |
| 4,819,751 | 4/1989 | Shimada et al. . |
| 4,892,519 | 4/1989 | Songer et al. . |
| 4,955,895 | 9/1990 | Sugiyama et al. . |
| 5,032,113 | 7/1991 | Burns . |
| 5,061,273 | 10/1991 | Yock . |
| 5,085,636 | 2/1992 | Burns . |
| 5,100,381 | 3/1992 | Burns . |
| 5,129,887 | 7/1992 | Euteneuer et al. . |
| 5,135,487 | 8/1992 | Morrill et al. . |
| 5,378,237 | 1/1995 | Boussignac et al. ................... 606/194 |
| 5,423,754 | 6/1995 | Cornelius et al. . |
| 5,425,712 | 6/1995 | Goodin . |
| 5,545,209 | 8/1996 | Roberts et al. ......................... 606/108 |
| 5,759,191 | 6/1998 | Barbere ................................... 606/194 |

FOREIGN PATENT DOCUMENTS

| | | |
|---|---|---|
| 0 213 752 | 3/1987 | European Pat. Off. . |
| WO 84/01513 | 4/1984 | WIPO . |
| WO 88/04560 | 6/1988 | WIPO . |

OTHER PUBLICATIONS

Promotional Sheet for Probe Balloon–On–A–Wire Dilatation System, distributed by USCI Division, C.R. Bard, Inc. (1/1989).

Primary Examiner—Michael Buiz
Assistant Examiner—Kevin Truong
Attorney, Agent, or Firm—Sterne, Kessler, Goldstein & Fox PLLC

[57] ABSTRACT

A balloon dilatation catheter used for percutaneous transluminal coronary angioplasty includes an inner tube and an outer tube. The anchor joint of the inner tube and outer tube is permit distal movement of the inner tube with respect to the outer tube while precluding proximal movement of the inner tube with respect to the outer tube. The outer tube is not immovably secured to the inner tube but, rather, may be slidably disposed on the inner tube. The distal end of the outer tube may be tapered to reduced diameter that permits the tapered portion to move longitudinally with respect to the inner tube. The inner tube is provided with an abutment member against which an abutment surface to the outer tube may abut.

14 Claims, 6 Drawing Sheets

ANCHOR JOINT FOR COAXIAL BALLOON DILATATION CATHETER

FIELD OF THE INVENTION

This invention relates to catheters and, particularly, to balloon dilatation catheters, including those used in percutaneous transluminal coronary angioplasty.

BACKGROUND OF THE INVENTION

Percutaneous transluminal coronary angioplasty (PTCA) is a procedure by which a balloon dilatation catheter is inserted into and manipulated within a patient's coronary arteries to unblock an obstruction (a stenosis) in the artery. Typically, the catheter is about 150 cm long and is inserted percutaneously into the patient's femoral artery in the region of the groin. The catheter then is advanced upwardly through the patient's arteries to the heart where, with the aid of a guidewire, the catheter is guided into the coronary artery where it can be controlled to perform the angioplasty procedure, described below.

In one type of balloon dilatation catheter, the catheter has two lumens. One lumen, for inflation and deflation of the balloon, extends from a fitting at the proximal end of the catheter and opens distally into the interior of the balloon. The balloon is inflated with a liquid and is deflated by aspirating the liquid from the balloon through the inflation/deflation lumen. The second lumen extends from another fitting at the proximal end of the catheter through the catheter and is open at the distal tip of the catheter shaft. The second lumen is adapted to receive a guidewire, such as a steerable small diameter guidewire. The first and second lumens may be arranged either in a parallel arrangement, in which the lumens are disposed side-by-side, or may be arranged in a coaxial manner in which one lumen is of a lesser diameter and is disposed within the other, larger diameter, lumen.

In a conventional coaxial PTCA balloon dilatation catheter, the elongate catheter shaft is formed from an inner tube and a coaxial outer tube. The inner tube extends from the proximal end fully to the distal end of the catheter and terminates in an open distal outlet. The lumen extending through the inner tube serves as a guidewire lumen. The outer tube extends from the proximal end of the catheter and terminates short of the distal end of the inner tube. The dilatation balloon is mounted on the distal end of the catheter with its proximal end adhesively attached to the distal end of the outer tube and the distal end of the balloon being adhesively attached to the distal end of the inner tube. The annular lumen defined between the inner tube and the outer tube communicates with the interior of the balloon and serves as the inflation/deflation lumen.

In a typical procedure, the guidewire is preliminarily loaded into the catheter and the assembly is inserted into a previously percutaneously placed guide catheter that extends to the region of the patient's heart and terminates at the entrance to the coronary arteries. The assembly of the balloon angioplasty catheter and the steerable guidewire is advanced through the guide catheter to the entrance to the coronary arteries. The guidewire then is projected into the coronary arteries and is steered by manipulation from its proximal end, while being observed under a fluoroscope, until the guidewire passes through the stenosis in the artery. Once the guidewire is in place, the balloon dilatation catheter is advanced over the guidewire, being guided directly to the stenosis to place the balloon within the region of the stenosis. Once in place, the balloon is inflated under substantial pressure to dilate the stenosis.

The anatomy of human vasculature, including the coronary arteries, varies widely from patient to patient. Often a patients coronary arteries are irregularly shaped and highly tortuous. The tortuous configuration of the arteries may present difficulties to the physician in properly placing the guidewire and then advancing the catheter over the guidewire. A highly tortuous coronary anatomy typically will present considerable resistance to advancement of the catheter over the guidewire. With certain types of catheter construction, the increased resistance may tend to cause portions of the catheter to collapse or buckle axially. For example, in a catheter having a shaft formed from inner and outer coaxial tubes, the balloon is mounted to the distal ends of the tubes. There may be a tendency for the tubes to telescope axially when presented with an increased resistance. The telescoping of the tubes will tend to draw the ends of the balloon together slightly but sufficiently to cause the balloon to become bunched up as it is forced through the stenosis because the length of the balloon will become shorter than when the coaxial tubes are in their normal, non-telescoped position. The bunching up of the balloon makes it more difficult for the balloon to be pushed into the stenosis.

The problems associated with the telescoping of the inner and outer tubes and the bunching of the balloon have been addressed by providing an anchor joint for to anchoring the distal end of the outer tube to the inner tube at a location in the distal region of the catheter. By preventing the telescoping of the inner and outer tubes, the length of the balloon does not contract, and bunching of the balloon is avoided. Such an anchor joint is illustrated in FIG. 1, taken from U.S. Pat. No. 5,759,191 shown in FIG. 1, the catheter is of coaxial construction with a annular space 20 forming the inflation lumen for the catheter. Inflation fluid annular space 20 through holes or other suitable openings 22 formed in the outer tube 12 to inflate the balloon.

The inner tube 10 has a guidewire lumen 24 to receive a guidewire used in a conventional manner. In FIG. 1, an inner tube 10 is shown as anchored to the outer tube 12 at an anchor joint 16 at the distal end 14 of the outer tube. The joint may be in the form of a ring-like spacer. The ring-like spacer 16 may be replaced by other means to join the outer and inner tubes, such as a weld or a tapering of the diameter of the tube 12 in the region of its distal end to a diameter about the diameter of the inner tube. Gluing or other well known means to join the distal end 14 of the outer tube to the inner tube 10 may be used to secure the tapered portion of the outer tube to the inner tube. By anchoring of the inner tube 10 to the outer tube 12, the balloon 18, when encountering a stenosis or other blockage within the arterial system of the patient, will resist bunching up and will substantially maintain its full length.

The catheter described in U.S. Pat. No. 5,759,191 improved on the prior art by anchoring the distal end of the outer tube to the inner tube. This arrangement increases the column strength and resists axial buckling of the catheter. The relative axial movement and telescopic buckling of the inner tube within the outer tube is avoided when the distal end of the catheter meets substantial resistance to advancement, as when crossing a difficult stenosis or negotiating tightly curved coronary arteries. Because the outer and inner tubes are affixed to one another, the inner tube cannot move, relative to the outer tube, either in a distal or a proximal direction.

It has been discovered that with some catheters, anchoring of the distal end of the outer tube to the inner tube may produce an undesirable side effect. In particular, this may occur with those coaxial balloon dilatation catheters that have balloons formed from a material that stretches more than conventional polyethylene terephthalate (PET). Such compliant balloons will tend to stretch somewhat more in both radial and longitudinal directions when inflated, particularly at higher inflation pressure of the order of 8 atmospheres and above. The longitudinal stretching of the balloon imposes a tension load on that portion of the inner tube that extends between the anchor joint and the distal connection of the balloon at the distal tip of the inner tube. Because the balloon typically will be formed from a material that is more elastic than that from which the inner tube is formed, the distal tip segment of the inner tube may be stretched beyond its elastic limit when the compliant balloon is inflated. Consequently, when the balloon is deflated and returns elastically toward its smaller dimensions, the tip segment of the inner tube may remain in its stretched configuration. Thus, when the balloon contracts toward its original dimensions it will apply a compressive load on the tip segment and may cause the tip segment to bend as suggested in FIG. 2.

As shown in FIG. 2, the inner tube 10 is bent within the balloon 18, and is shown as being distorted over length 24. This distortion of the length 24 can cause additional friction due to the band, for a guidewire moving within the distal portion of the inner tube 10 and this could hinder performance. The distortion of the portion 24 can be so great as to cause the portion 24 of the inner tube to lie against the inner wall of the balloon and affect the shape of the collapsed balloon.

SUMMARY OF THE INVENTION

In order to avoid the distortion of the inner tube 20 as illustrated in FIG. 2, the anchor joint of the inner tube and outer tube shown in FIG. 1 is modified to permit distal movement of the inner tube with respect to the outer tube while precluding proximal movement of the inner tube with respect to the outer tube. The outer tube is not immovably secured to the inner tube but, rather, may be slidably disposed on the inner tube. The distal end of the outer tube may be tapered to a reduced diameter that permits the tapered portion to move longitudinally with respect to the inner tube. The inner tube is provided with an abutment member against which an abutment surface of the outer tube may abut. The abutment member may be located distally of the distal end of the tapered outer tube against which the end of the tapered tube can abut. That allows the inner tube to move distally relative to the outer tube but prevents relative movement of the inner tube in a proximal direction. Thus, when the compliant balloon is inflated the entire length of the inner tube is available to absorb the tension load of the stretched inflated balloon. Because the tension load is distributed over a much longer length inner tube, the inner tube is not strained beyond its elastic limit and will not become permanently distorted. However, since the presence of the fixed abutment on the inner tube precludes movement of the outer tube beyond that abutment, the catheter maintains the desirable pushability achieved with the fixed anchor joint illustrated in FIGS. 1 and 2.

It is among the objects of the invention to provide an improved coaxial balloon dilatation catheter construction.

Another object of the invention is to provide a PTCA catheter having a coaxial construction in which there is a reduced tendency for the balloon to become bunched as it is advanced through a resisting stenosis.

Another object of the invention is to provide an angioplasty catheter having a coaxial construction and a compliant balloon that avoids a tendency of the inner tube of the catheter shaft to become permanently distorted after an inflation of a relatively compliant balloon.

A further object of the invention is to provide a coaxial balloon dilatation catheter of the type described in which the inner tube of the catheter shaft is free to move distally relative to the outer shaft but is prevented from moving in a proximal direction.

DESCRIPTION OF THE DRAWINGS

The foregoing and other objects and advantages of the invention will be appreciated more fully from the following further description thereof, with reference to the accompanying drawings wherein.

DESCRIPTION OF THE ILLUSTRATIVE EMBODIMENTS

Figure 3A:
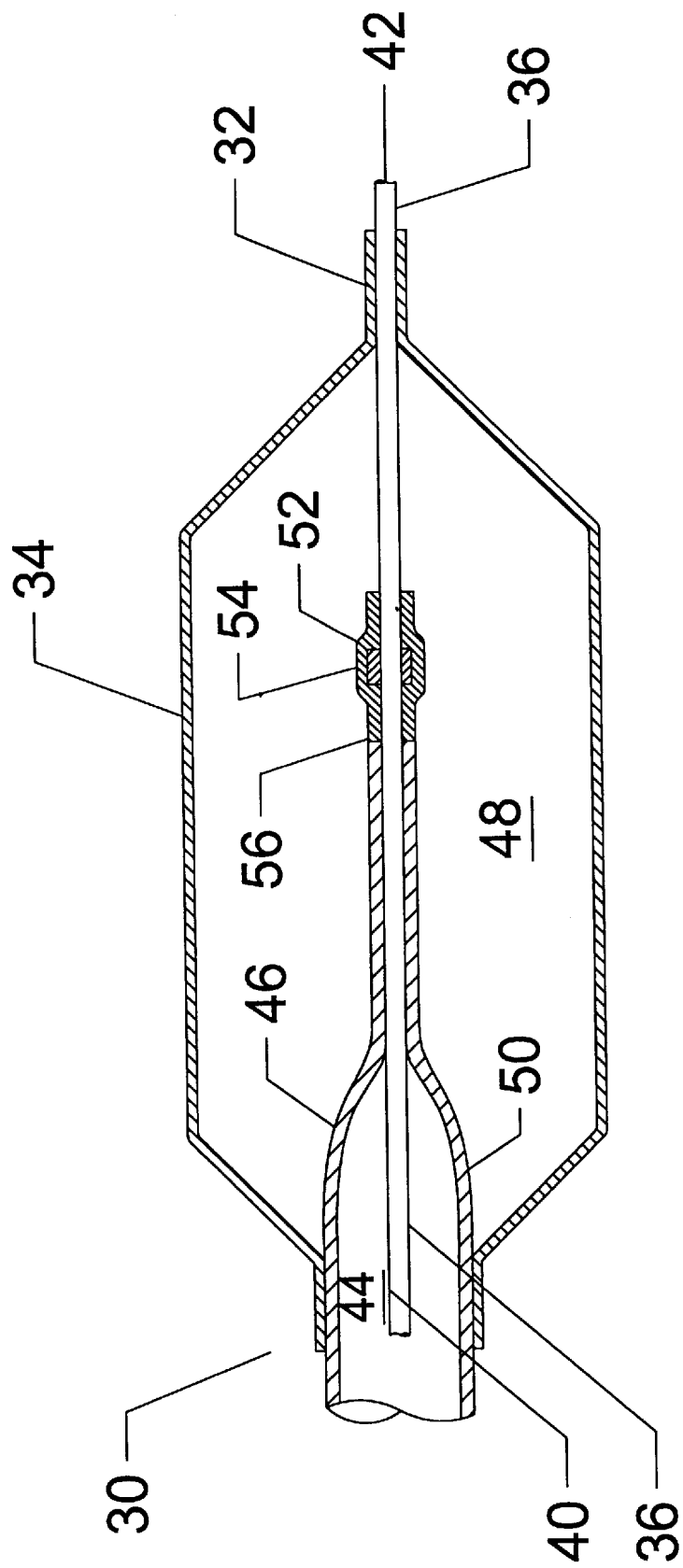
FIG. 3a illustrates, diagrammatically, a first embodiment of the distal region of a catheter having an anchor joint of the present invention with the balloon deflated.

As shown in FIG. 3a, the catheter includes a shaft, indicated generally at 30. The catheter has a proximal end (to the left of FIG. 3A) and distal end 32. A dilatation balloon 34 is mounted to the distal end of the shaft 30. In the illustrative embodiment of the invention, the catheter shaft 30 is formed from a pair of coaxial tubes, including an inner tube 36 and an outer tube 38. The tubes 36, 38 may be formed from polyethylene, with the inner tube being formed, for example, from high density polyethylene and the outer tube being formed from linear low density polyethylene. By way of example, the catheter may be of the order of 150 cm long. The inner tube may have an outer diameter of about 0.027" and a wall thickness of the order of 0.003". The outer tube may have an outer diameter of the order of 0.045 with a wall thickness of the order of 0.005. The inner tube 36 defines an inner lumen 40 adapted to receive a guidewire in the conventional manner of over-the-wire dilatation catheters. The inner tube 36 extends fully to the distal tip of the catheter. An annular inflation lumen 44 is defined between the inner tube 36 and the outer tube 38.

The guidewire lumen 40 extends from the proximal end of the catheter fully to the distal tip of the catheter and terminates in an outlet opening 42 through which a guidewire may extend. The guidewire may be manipulated from its proximal end in the conventional manner and may be steered through the coronary arteries to the branch of the coronary arteries where the stenosis is located. One or more apertures 46 formed within the portion of the outer tube 38 end located within the balloon 34 serve to direct inflation fluid from the annular inflation lumen 44 into the interior 48 of the balloon.

Figure 3B:
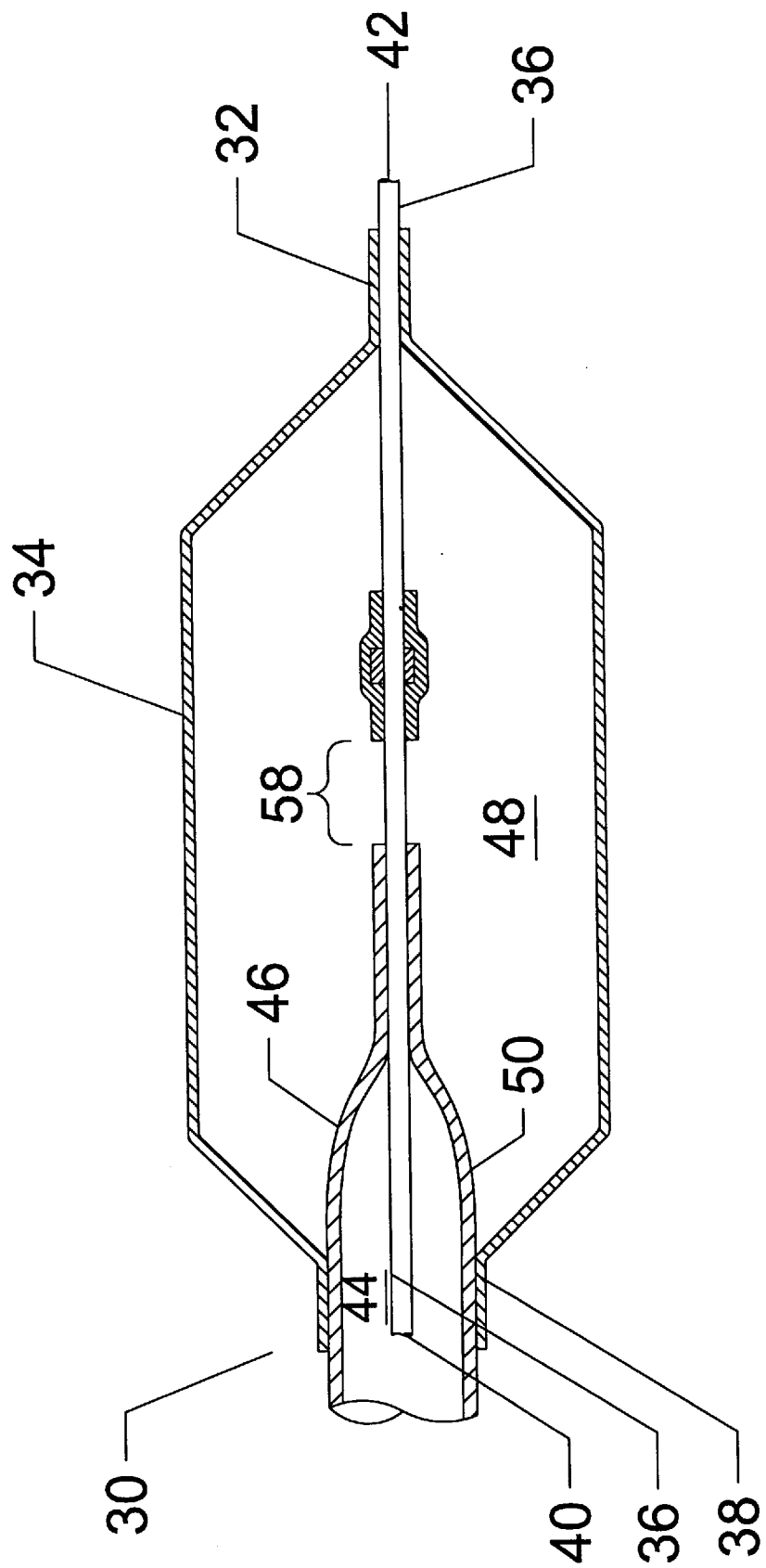
FIG. 3b illustrates, diagrammatically, the operation of the anchor joint of the present invention with the balloon inflated.

The outer tube 38 extends from the proximal end of the catheter 30 to a location short of the distal end of the inner tube 36 and may terminate within the balloon 34 as shown in FIG. 3a. In accordance with the invention, and as described further below, the distal end portion 50 of the outer tube 38 may be tapered to a diameter that enables the inner tube to slide inside the outer tube 36 at a location within the balloon. An abutment member 52, which also may be formed from polyethylene, is attached to the inner tube 36 so as to be permanently bonded, by suitable means well known in the art, to anchor element 52 on the inner tube. The abutment element 52 may also include a radiopaque marker band 54 to aid the physician in fluoroscopic location of the balloon. Although the abutment 52 is shown in FIGS. 3a and 3b approximately in the middle of the balloon, it is understood that its position within the balloon may be varied according to the particular design chosen. The outer tube may be considered as having an abutment surface that, as shown in FIG. 3a, abuts the abutment member 52 as indicated at 56. The abutment member 52 and abutment surface should be in engagement when the balloon is deflated, thereby preventing telescoping of the inner and outer tubes when the catheter is advanced. The outer tube 38, however, may move proximally of the abutment member 52, as explained below. Thus, in operation, the engagement of the outer tube 38 and the abutment member 52, services to anchor the tubes to provide pushability of both the inner and outer tubes as a unit while enabling the inner tube to move distally relative to the outer tube, as when a compliant balloon is pressurized with inflation liquid.

FIG. 3b illustrates the position of the outer tube 38 and the inner tube 36 when inflation fluid has been injected into the balloon and the balloon has stretched longitudinally. Upon inflation, the inner tube 36 may stretch so that its distal end moves distally with respect to the outer tube 38. Such movement causes a space to develop between the outer tube 38 and the abutment 52, as indicated by the numeral 58. When the balloon material is of a relatively compliant material, the balloon expands in a longitudinal as well as in a radial direction. The inner shaft 36 may then stretch distally to cause the proximal end 56 of the abutment 52 to shift to the spaced position of FIG. 3b. This freedom of movement prevents concentration of the stretching effect of the compliant balloon in the short distal segment of the inner tube 36 within the balloon, thus avoiding permanent distortion of the inner tube. Although with balloons constructed of PET material, having a smaller coefficient of expansion when inflated as compared to non-PET balloons, it may be sufficient to utilize the fixed anchor joint described in U.S. Pat. No. 5,759,191. The present improved anchor joint may be used with a PET balloon should there be a reason to compensate for longitudinal expansion of the balloon.

It should be understood that, although the drawings illustrate the invention with abutment member and abutment surface disposed within the balloon, the invention also may be practiced by locating an abutment member and a cooperative abutment surface at a location along the coaxial shaft that is proximal of the balloon. Preferably such shaft-contained abutment member and abutment surface should be disposed toward the distal portion of the catheter shaft so that an advancing force applied to the outer shaft will be transferred to the inner shaft at a location toward the distal end of the catheter.

Figure 4:
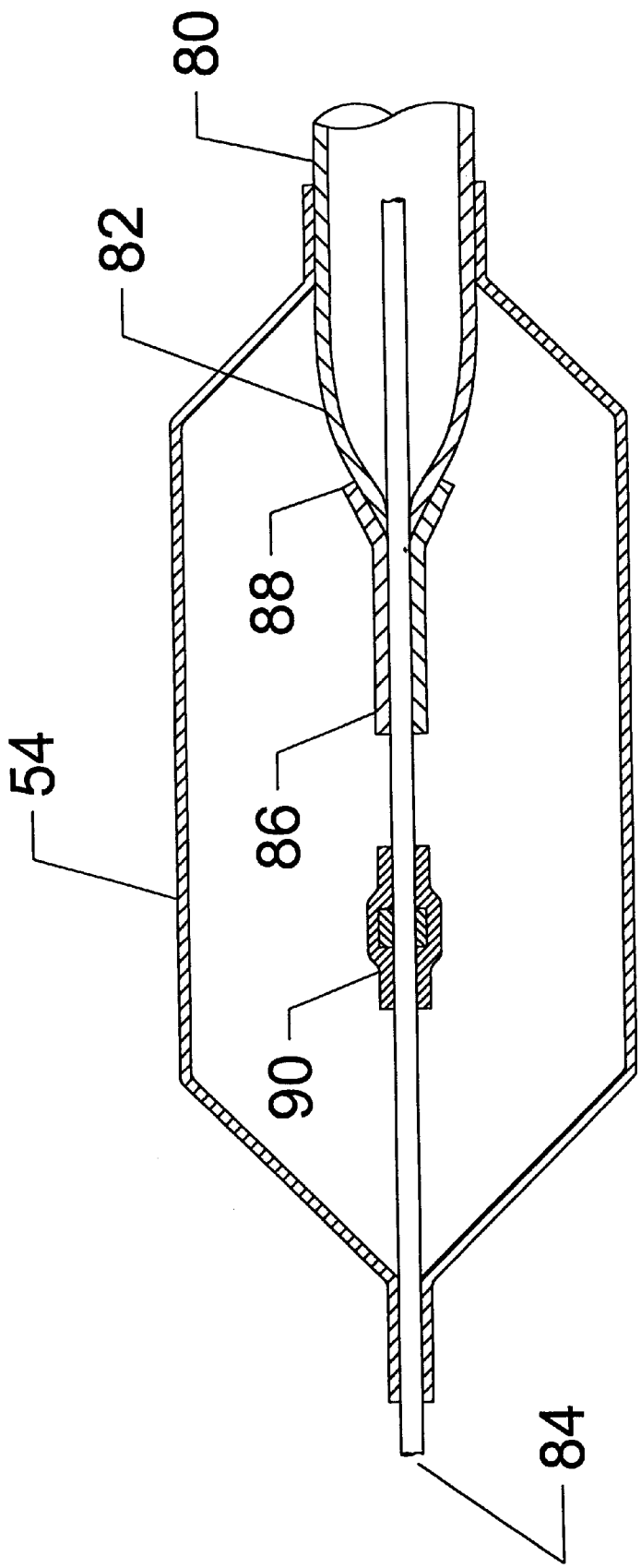
FIG. 4 illustrates, diagrammatically, a second embodiment of the anchor joint of the present invention.

FIG. 4 illustrates another embodiment of the present invention in which the outer tube 80 is tapered in a distal portion 82 within the balloon 54 to closely approximate (but be slightly larger than) the outer diameter of the inner tube 84. A flared tubular abutment member 86 is attached to the inner tube by suitable means well known to those skilled in the art with a flared proximally-facing shape 88 to abut against the tapered portion 82 of the outer tube 80. As in the embodiment in FIG. 3a, the flared tube 86 serves as an abutment between the outer tube and the inner tube to aid in pushability of the catheter shaft. However, the inner shaft 84 also is movable in a distal direction for the purpose described above with respect to FIG. 3a. A marker band 90 may be attached to the inner shaft at a position shown in FIG. 4.

Figure 5:
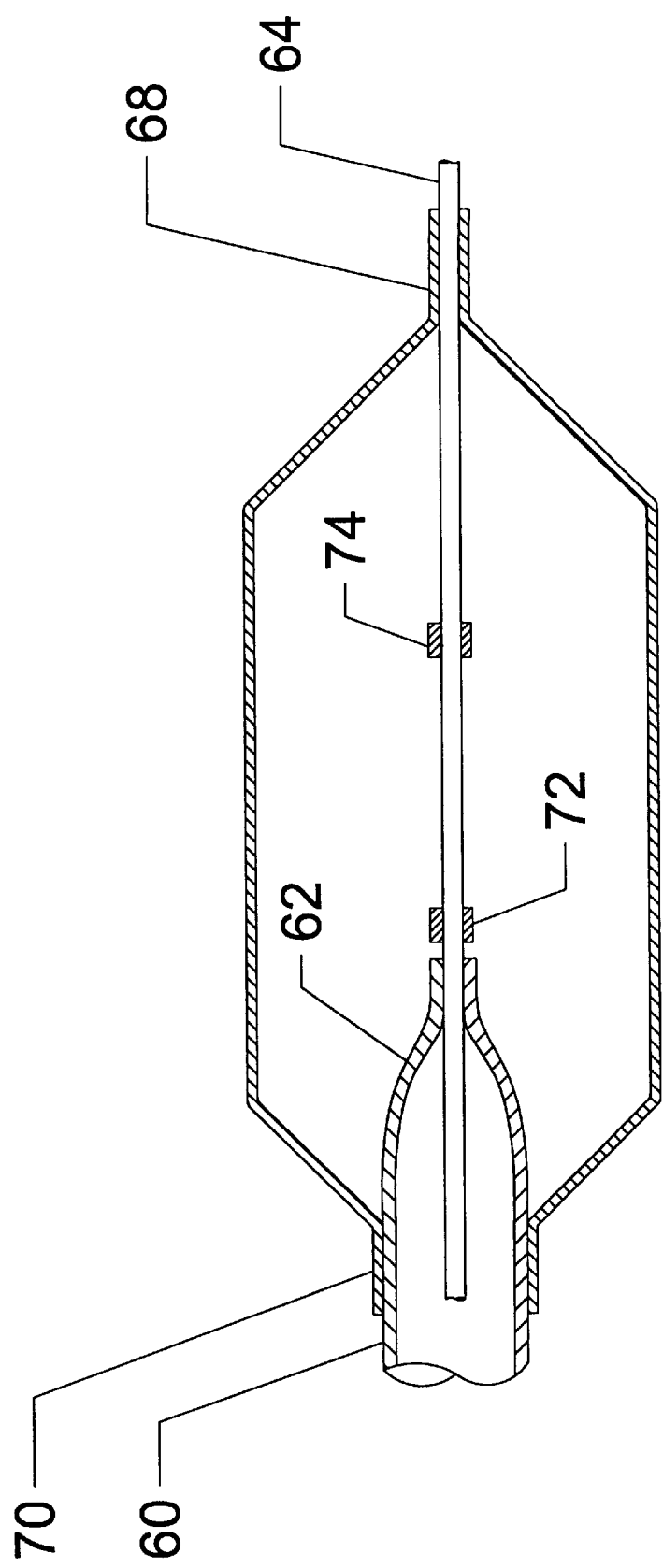
FIG. 5 illustrates, diagrammatically, a third embodiment of the anchor joint of the present invention.

FIG. 5 illustrates another embodiment of the present invention in which an outer tube 60 is tapered within the balloon at portion 62 to closely approximate the diameter of-the inner tube 64, as in FIG. 3a. A balloon is attached to the distal portion of the inner tube at 68 and to the distal portion of the outer tube 60 at 70. An abutment member 72 is permanently attached to the inner tube 64 in a manner described with respect to FIG. 3a. The abutment 72 provides a stop to assist in the pushability of the catheter through the patient's arterial system while allowing for a balloon expansion, as described with respect to the embodiment of FIG. 3a. A separate marker band 74 is shown attached to the inner tube 64. Thus, the position of the marker band 74 in the embodiment of FIG. 5 is not required to be the same as the position of the abutment member, as is shown in FIG. 3a in the event that it is desirable to mount the marker band at a position different from the position of the abutment member.

Thus, in the embodiments of FIGS. 3a, 4 and 5, the inner tube can slide relative to the outer tube in a distal direction but not in a proximal direction. The arrangement achieves the dual function of aiding in pushability and allowing for balloon expansion without the occurrence of inner tube distortion.

Figure 1:
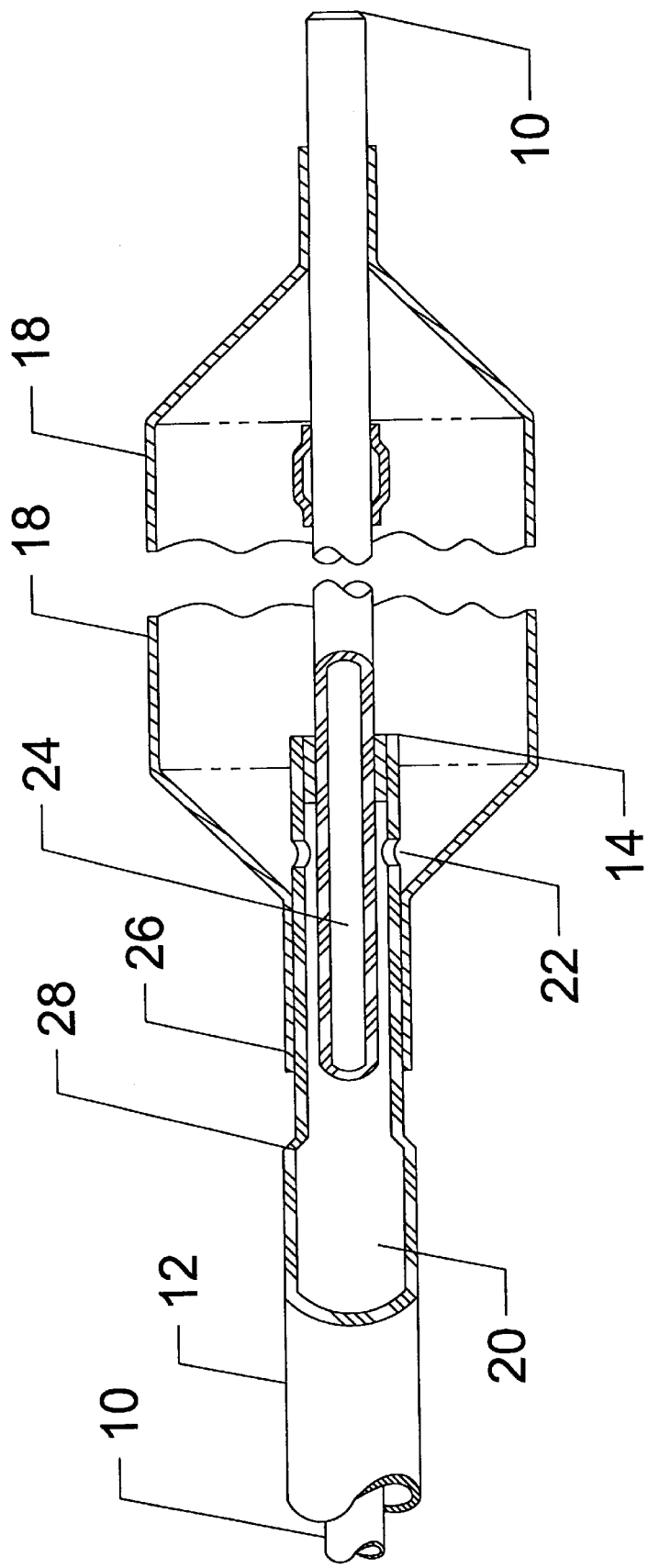
FIG. 1 is a diagrammatic illustration of a coaxial balloon dilatation catheter having a fixed anchor joint.
Figure 2:
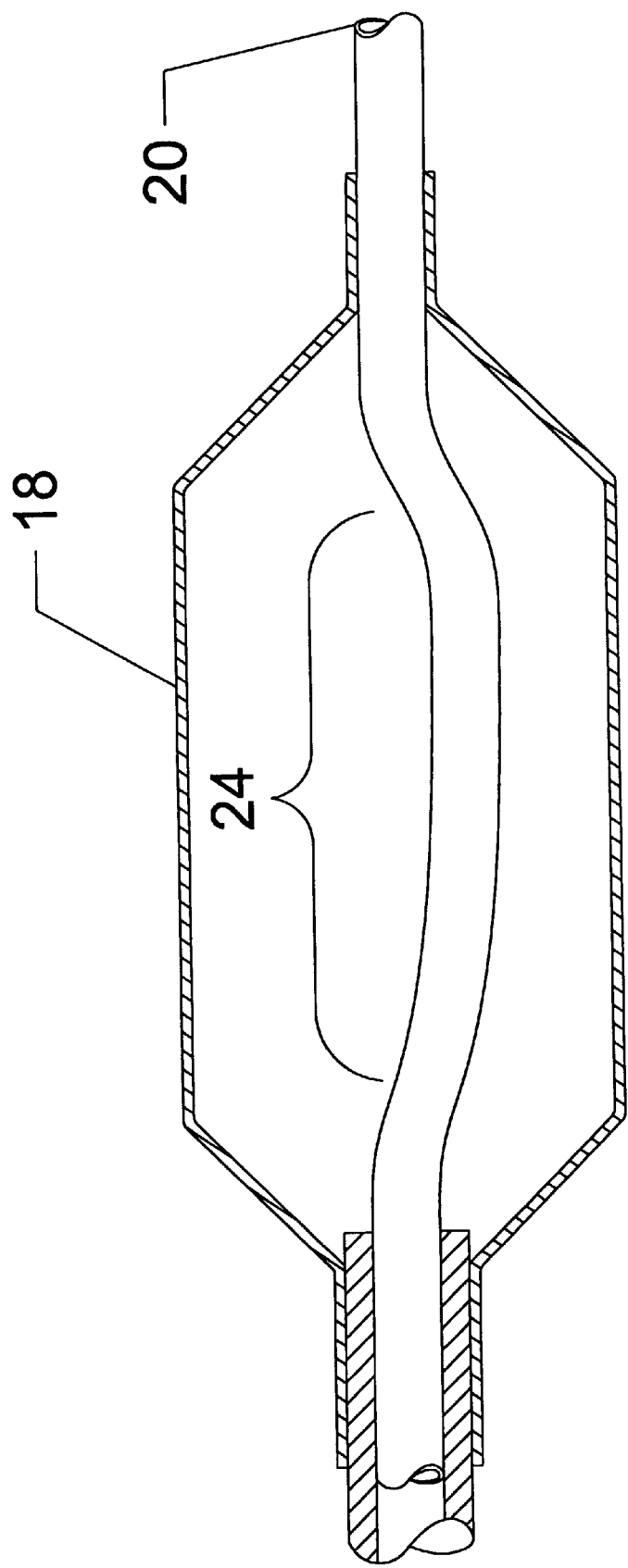
FIG. 2 is a diagrammatic illustration of inner tube distortion occurring with the device of FIG. 1.

From the foregoing, it will be appreciated that after the guidewire has been navigated to a desired location in the patient's vasculature the physician then will advance the catheter over and axially along the guidewire. Should the vascular anatomy present resistance, as by presenting one or both of a narrow difficult stenosis and tortuous path, the increased column strength resulting from anchoring the distal end of the outer tube 20 to the inner tube 18 in a manner described herein will increase the pushability of the catheter. The axial force applied to both the inner and outer tubes is available to push the catheter through the tortuous anatomy and/or the balloon through a difficult stenosis. With the foregoing arrangement, the tendency of the inner tube to telescope within the outer tube is avoided. As a consequence, the axial distance between the ends of the balloon is maintained and the balloon will not bunch up as it is pushed through a tight stenosis. In addition, the inner shaft may move relative to the outer shaft in a distal direction to account for longitudinal extension of the balloon when the balloon is inflated with inflation fluid. This arrangement prevents the distortion of the inner tube illustrated in FIG. 2 and described above.

The invention thus provides an improved coaxial catheter construction for a balloon dilatation catheter by which the column strength and resistance to telescopic buckling of the catheter, and particularly, of the inner tube and balloon of a coaxial catheter, is improved. The resulting catheter has increased pushability. Bunching up of the balloon is avoided and, due to the ability of distal movement of the inner tube, inner tube distortion is prevented. By providing movement of the inner tube distally relative to the outer tube, the entire length of the inner tube can absorb the stretch of the balloon rather than causing distortion to its distal portion.

It should be understood that the foregoing invention is intended merely to be illustrative thereof and that other embodiments, modifications and equivalents may be apparent to those skilled in the art without departing from its spirit.

Having thus described the invention what I desire to claim and secure by letters patent is:

1. A balloon dilatation catheter comprising:

an elongate catheter shaft having an inner tube and a surrounding outer tube, each tube having a distal region and a distal end, the inner tube being of smaller diameter than that of the outer tube and extending distally of the distal end of the outer tube, the inner and outer tubes being movable longitudinally with respect to each other;

the inner and outer tubes defining an annular inflation lumen therebetween, the inner tube defining a guidewire lumen therethrough;

an inflatable dilatation balloon having a proximal end and a distal end, the proximal end of the balloon being attached to the distal region of the outer tube, the distal end of the balloon being attached to the distal region of the inner tube at a distal connection;

the inner tube having an abutment member thereon, and the outer tube having an abutment surface engageable with the abutment member, the abutment member having a transverse dimension large enough tube engaged by the abutment surface of the outer tube, the abutment member being located longitudinally on the inner tube to enable the abutment surface of the outer tube to engage the abutment member to transfer a distally directed longitudinal force applied to the outer tube in a distal direction to the inner tube through the abutment member when the abutment surface of the outer tube is in engagement with the abutment member; and the annular inflation lumen being in communication with the interior of the balloon to enable the balloon to be inflated and deflated.

2. A balloon dilatation catheter as defined in claim 1 wherein the abutment surface of the outer tube is located at the distal end of the outer tube.

3. A balloon dilatation catheter as defined in claim 1 wherein the abutment surface comprises a distally facing surface defined at the distal extremity of the outer tube.

4. A balloon dilatation catheter as defined in claim 1 wherein the abutment member is located within the balloon.

5. A catheter as defined in claim 1 wherein the inflation lumen and the interior of the balloon are in communication by at least one aperture formed in a portion of the outer tube disposed within the balloon.

6. A catheter as defined in claim I in which the distal end of the outer tube is tapered within the inflatable dilatation balloon to an inner diameter slightly larger than the outer diameter of the inner tube.

7. A catheter as defined in claim 1 further comprising a radiopaque marker band in the abutment member.

8. A catheter as defined in claim 1 wherein the abutment member comprises a tube which is flared in a proximally facing direction and the outer tube is tapered inward in its distal portion, the distal portion of the outer tube and the flared end of the tube abutting with one another when the balloon is in a non-inflated condition.

9. A catheter as defined in claim 8 further comprising a marker band of radiopaque material affixed to the inner tube within the inflatable balloon.

10. A catheter as defined in claim 1 wherein the balloon is expandable longitudinally when it is inflated.

11. A catheter as defined in claim 10 further comprising the abutment member and abutment surface being located to be in engagement with each other before the balloon is inflated.

12. A catheter as defined in claim 11 further comprising the inner tube being constructed so that when the balloon is extended longitudinally in response to inflation of the balloon, the inner tube will not be tensioned beyond its elastic limit.

13. A catheter as defined in claim 10 wherein the balloon is constructed of a compliant material that expands longitudinally when inflated.

14. A catheter as defined in claim 1 wherein the balloon is constructed of a compliant material which expands longitudinally when inflated.

* * * * *